(12) United States Patent
Jones et al.

(10) Patent No.: US 9,004,064 B2
(45) Date of Patent: *Apr. 14, 2015

(54) DELIVERY DEVICE AND RELATED METHODS

(71) Applicant: Manta Devices, LLC, Roslindale, MA (US)

(72) Inventors: Andrew Jones, Roslindale, MA (US); Richard L. Miller, Needham, MA (US)

(73) Assignee: Manta Devices, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/047,369

(22) Filed: Oct. 7, 2013

(65) Prior Publication Data

US 2014/0034053 A1  Feb. 6, 2014

Related U.S. Application Data

(63) Continuation of application No. 12/688,852, filed on Jan. 15, 2010, now Pat. No. 8,550,074.

(60) Provisional application No. 61/145,008, filed on Jan. 15, 2009, provisional application No. 61/285,161, filed on Dec. 9, 2009.

(51) Int. Cl.
*A61M 16/00* (2006.01)
*A61M 15/00* (2006.01)

(52) U.S. Cl.
CPC ....... *A61M 15/0028* (2013.01); *A61M 15/0045* (2013.01); *A61M 15/0041* (2014.02); *A61M 15/0043* (2014.02); *A61M 15/0061* (2014.02); *A61M 2206/16* (2013.01)

(58) Field of Classification Search
CPC .............. A61M 15/0028; A61M 15/0061; A61M 15/0043; A61M 15/0045; A61M 15/0041
USPC ............ 604/23–26; 128/203.12, 203.13, 128/203.14, 203.15
See application file for complete search history.

(56) References Cited

U.S. PATENT DOCUMENTS

| | | | |
|---|---|---|---|
| 2,307,986 A | 1/1943 | Bolte et al. | |
| 2,860,638 A | 11/1958 | Bartolomeo | |
| 2,974,787 A | 3/1961 | Cooper | |
| 3,888,253 A | 6/1975 | Watt et al. | |
| 3,964,482 A | 6/1976 | Gerstel et al. | |
| 4,249,526 A | 2/1981 | Dean et al. | |

(Continued)

FOREIGN PATENT DOCUMENTS

| | | |
|---|---|---|
| DE | 4400083 A1 | 7/1995 |
| EP | 0407276 | 1/1991 |

(Continued)

OTHER PUBLICATIONS

Partial International Search Report from related International Application No. PCT/US2008/008303 dated Dec. 4, 2008.

(Continued)

*Primary Examiner* — Manuel Mendez
(74) *Attorney, Agent, or Firm* — Grossman Tucker Perreault & Pfleger, PLLC

(57) ABSTRACT

A delivery device that includes a cutter for opening a barrier layer to provide fluid access to a dose chamber, and a diverting structure for direct air flow toward the dose chamber.

19 Claims, 20 Drawing Sheets

(56) References Cited

U.S. PATENT DOCUMENTS

| | | |
|---|---|---|
| 4,338,931 A | 7/1982 | Cavazza |
| 4,601,896 A | 7/1986 | Nugent |
| 5,035,237 A | 7/1991 | Newell et al. |
| 5,167,242 A | 12/1992 | Turner et al. |
| 5,239,993 A | 8/1993 | Evans |
| 5,320,714 A | 6/1994 | Brendel |
| 5,388,572 A | 2/1995 | Mulhauser et al. |
| 5,400,808 A | 3/1995 | Turner et al. |
| 5,476,093 A | 12/1995 | Lankinen |
| 5,501,236 A | 3/1996 | Hill et al. |
| 5,562,918 A | 10/1996 | Stimpson |
| 5,596,982 A | 1/1997 | Blaha-Schnabel |
| 5,622,166 A | 4/1997 | Eisele et al. |
| 5,647,349 A | 7/1997 | Ohki et al. |
| 5,669,378 A | 9/1997 | Pera et al. |
| 5,673,793 A | 10/1997 | Seidler |
| 5,775,320 A | 7/1998 | Patton et al. |
| 5,893,452 A | 4/1999 | De Nervo |
| 5,921,237 A | 7/1999 | Eisele et al. |
| 5,947,117 A | 9/1999 | Herold |
| 5,954,204 A | 9/1999 | Grabowski |
| 6,029,663 A | 2/2000 | Eisele et al. |
| 6,089,228 A | 7/2000 | Smith et al. |
| 6,209,538 B1 | 4/2001 | Casper et al. |
| 6,230,707 B1 | 5/2001 | Horlin |
| 6,234,169 B1 | 5/2001 | Bulbrook et al. |
| 6,328,034 B1 | 12/2001 | Eisele et al. |
| 6,347,629 B1 | 2/2002 | Braithwaite |
| 6,401,712 B1 | 6/2002 | Von Schuckmann |
| 6,427,688 B1 | 8/2002 | Ligotke et al. |
| 6,443,152 B1 | 9/2002 | Lockhart et al. |
| 6,443,307 B1 | 9/2002 | Burridge |
| 6,550,477 B1 | 4/2003 | Casper et al. |
| 6,595,203 B1 | 7/2003 | Bird |
| 6,595,210 B2 | 7/2003 | Ohki et al. |
| 6,655,381 B2 | 12/2003 | Keane et al. |
| 6,681,768 B2 | 1/2004 | Haaije de Boer et al. |
| 6,748,947 B2 | 6/2004 | Keane et al. |
| 6,810,872 B1 | 11/2004 | Ohki et al. |
| 6,871,646 B2 | 3/2005 | Keane et al. |
| 6,932,082 B2 | 8/2005 | Stein |
| 6,941,947 B2 | 9/2005 | Young et al. |
| 6,971,384 B2 | 12/2005 | Gieschen et al. |
| 7,025,056 B2 | 4/2006 | Eason et al. |
| 7,025,057 B2 | 4/2006 | Chawla |
| 7,143,765 B2 | 12/2006 | Asking et al. |
| 7,401,713 B2 | 7/2008 | Ede et al. |
| 7,617,822 B2 | 11/2009 | De Boer et al. |
| 8,109,267 B2 | 2/2012 | Villax et al. |
| 8,550,074 B2 * | 10/2013 | Jones et al. .............. 128/203.21 |
| 2001/0027790 A1 | 10/2001 | Gieschen et al. |
| 2001/0029948 A1 | 10/2001 | Ingle et al. |
| 2002/0006316 A1 | 1/2002 | Schuler et al. |
| 2002/0020408 A1 | 2/2002 | Knauer |
| 2002/0092523 A1 | 7/2002 | Connelly et al. |
| 2002/0170560 A1 | 11/2002 | Young et al. |
| 2003/0034271 A1 | 2/2003 | Burridge |
| 2004/0107963 A1 | 6/2004 | Finlay et al. |
| 2004/0182387 A1 | 9/2004 | Steiner et al. |
| 2004/0206350 A1 | 10/2004 | Alston et al. |
| 2004/0211419 A1 | 10/2004 | Eason et al. |
| 2004/0236282 A1 | 11/2004 | Braithwaite |
| 2005/0022813 A1 | 2/2005 | Alston |
| 2005/0188988 A1 | 9/2005 | Poole et al. |
| 2006/0005833 A1 | 1/2006 | Gieschen et al. |
| 2006/0108877 A1 | 5/2006 | Tegel |
| 2006/0169278 A1 | 8/2006 | Djupesland et al. |
| 2007/0023381 A1 | 2/2007 | Cerveny |
| 2007/0074721 A1 | 4/2007 | Harmer et al. |
| 2007/0151562 A1 | 7/2007 | Jones et al. |
| 2008/0251072 A1 | 10/2008 | Lulla et al. |
| 2008/0314384 A1 | 12/2008 | Harris et al. |
| 2009/0250057 A1 | 10/2009 | Wachtel |
| 2009/0308392 A1 | 12/2009 | Smutney et al. |
| 2009/0321295 A1 | 12/2009 | Ede et al. |

FOREIGN PATENT DOCUMENTS

| | | |
|---|---|---|
| EP | 1844809 A1 | 10/2007 |
| GB | 1211168 | 11/1967 |
| GB | 2179260 A | 3/1987 |
| GB | 2375310 A | 11/2002 |
| GB | 2405798 A | 3/2005 |
| GB | 2420982 A | 6/2006 |
| JP | 08-103499 A | 4/1996 |
| WO | WO 90/07351 A1 | 7/1990 |
| WO | WO 96/09085 | 3/1996 |
| WO | WO 99/06092 A1 | 2/1999 |
| WO | WO 01/05675 A1 | 1/2001 |
| WO | WO 01/26720 A1 | 4/2001 |
| WO | WO 01/56640 A1 | 9/2001 |
| WO | WO 01/85097 | 11/2001 |
| WO | WO 02/098495 A1 | 12/2002 |
| WO | WO 03/000326 A1 | 1/2003 |
| WO | WO 03/015857 A1 | 2/2003 |
| WO | WO 2004/103446 A1 | 12/2004 |
| WO | WO 2005/002654 A3 | 1/2005 |
| WO | WO 2005/025656 A1 | 3/2005 |
| WO | WO 2005/030305 A1 | 4/2005 |
| WO | WO 2006/066910 A1 | 6/2006 |
| WO | WO 2007/007110 A1 | 1/2007 |
| WO | WO 2009/092650 | 7/2009 |

OTHER PUBLICATIONS

International Preliminary Report on Patentability from corresponding International Application No. PCT/US2010/000090 dated Jul. 19, 2011.

* cited by examiner

CLOSED POSITION

DELIVERY DEVICE AND RELATED METHODS

RELATED APPLICATIONS

This application is a continuation of U.S. patent application Ser. No. 12/688,852, filed Jan. 15, 2010, which claims the benefit of U.S. Provisional Patent Application Ser. Nos. 61/145,008, filed Jan. 15, 2009 and 61/285,161, filed Dec. 9, 2009. Each of these applications is incorporated herein by reference in its entirety.

RELATED ART

Medicament in the form of dry powder may be delivered directly into the lungs, such as by inhalation. The powder may be prepared as an incipient formulation, a neat formulation, a blended formulation, or any combinations thereof. Administering medicament in this manner may prove less invasive than other drug delivery techniques, such as hypodermic injections. Direct inhalation of medicament may also allow smaller doses to be used to achieve results similar to those of the same drug taken orally. Inhalation may also help avoid undesirable side effects associated with administering drugs orally or by injection.

SUMMARY

Aspects of the invention relate to devices, systems, and methods that are used to deliver a dose of a drug/medicament (such as a liquid and/or a powder). The devices, systems and methods may include features that allow the drug to be protected (e.g., from contamination and/or degradation) prior to use, and to be delivered in a metered manner. For example, in some embodiments, the drug is isolated to a selected volume/dose chamber with a barrier, such as a foil layer that prevents the ingress of contaminants and the egress of a dose from dose chamber prior to use. As a result, the initial location of the drug dose is known, and the dose may be delivered predictably from the same starting point.

According to one aspect, a delivery device includes a primary air pathway having an upstream portion and a downstream portion. A dose chamber has an opening that, when opened, places the dose chamber and the primary pathway in fluid communication at a position between the upstream portion and the downstream portion. A cover, when in a first position over the opening, closes fluid communication between the dose chamber and the primary air pathway. The cover moves to a second position to selectively open fluid communication between the dose chamber and the primary air pathway through the opening, and is positioned to divert air to the dose chamber from the upstream portion of the air pathway when in the second position.

According to another aspect, a delivery device includes a primary air pathway and a dose chamber having an opening and a curved interior surface. A first portion of the curved interior surface is positioned to receive air from the air pathway and a second portion of the curved interior surface is positioned to direct air toward the air pathway from the dose chamber. A moisture barrier covers the opening. A cutter moves from a first position to a second position to break the moisture barrier to open fluid communication between the dose chamber and the primary air pathway. The cutter is positioned to direct air to the dose chamber from the air pathway and to prevent a portion of air directed toward the air pathway by the second portion of the curved interior surface from reaching the air pathway, when in the second position.

According to yet another aspect, a delivery device includes a primary air pathway and a dose chamber having an opening. A moisture barrier covers the opening. A cutter that is on the dose chamber side of the barrier moves, when actuated, to break the moisture barrier to selectively open fluid communication between the dose chamber and the primary air pathway through the opening. The cutter is positioned to divert air to the dose chamber from the air pathway when in the second position.

According to yet another aspect, a delivery device includes a primary air pathway having an upstream portion and a downstream portion. A dose chamber has an opening that, when opened, places the dose chamber and the primary pathway in fluid communication at a position between the upstream portion and the downstream portion. A moisture barrier covers the opening. A cutter moves, when actuated, to break the moisture barrier selectively opening fluid communication between the dose chamber and the primary air pathway. The cutter protrudes at least partially into the primary air pathway to divert air to the dose chamber from the upstream portion of the air pathway when moved to the second position.

In certain aspects of the invention, a dose of drug may be dispersed, fluidized, and/or metered from its initial location in the delivery device. The drug may be delivered as fine particles, mitigating, for example, the occurrence of large clump(s), which may reduce therapeutic effectiveness of the drug. A satisfactory combination of dispersion, fluidization and metering may also enhance drug delivery, for example, by allowing substantially all of the drug dose to be delivered, which may increase safety and lower cost and waste.

The following terms are used throughout this application and have the following definitions.

The term "active" refers to the use of one or more external mechanisms and/or forces in addition to the patient's respiration.

The term "passive" refers to the use of the patient's respiration.

Other aspects, features and advantages will be apparent from the description of the following embodiments and from the claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Delivery devices described herein include one or more dose chambers for storing and delivering a dose of a substance, such as a powdered medicament, to a subject. The dose chamber may be placed in fluid communication with an air pathway to ready the medicament for delivery to the subject. Air is drawn or pushed through the air pathway and at least a portion of the air enters the dose chamber to entrain medicament in a metered manner. Air then reenters the air pathway from the dose chamber, laden with powder from the dose chamber, and moves towards an outlet of the delivery device to a subject.

According to one aspect, a delivery device includes an air pathway and a dose chamber having a cover that, in a first position, holds a dose in the dose chamber. The cover, when actuated, pivots to a second position where the cover may direct air into the dose chamber to entrain dose before returning to the air pathway to deliver the dose to a subject.

According to another aspect, a delivery device has a dose chamber with an opening that is sealed by a barrier to prevent the ingress of moisture and contaminants to the chamber and/or the egress of dose from the chamber. A cutter or cover of the device may move, such as by pivoting, from a first position to a second position to break the moisture barrier and open fluid communication to an air pathway. When in the second position, the cutter or cover may promote recirculation of air through the dose chamber by being positioned in front of the path of air that leads back to the air pathway from the dose chamber.

According to another aspect, a cutter may be positioned on a dose chamber side of the barrier of a delivery device. The cutter may move, such as by pivoting or translating, when actuated, to break the moisture barrier and open fluid communication between the dose chamber and the primary air pathway.

Turn now to the figures, and initially FIGS. 1*a* and 1*b*, which show a cross-sectional view of a delivery device, according to one illustrative embodiment. The device includes an air pathway 22 and a sealed dose chamber 34 that contains a dose 36 of powdered medicament, or other substance to be delivered through an opening to the air pathway 22 and eventually to a subject. The chamber, as illustrated in the embodiment of FIGS. 1*a* and 1*b*, is generally cylindrical in shape, although other shapes are also possible. The chamber is formed of an upper housing 40 and a lower housing 42 that may be formed of injection molded plastic, among other materials. A barrier 28 is mounted about the opening 36 to provide a selectively openable, air impermeable seal that prevents in the ingress of moisture or contaminants to the dose chamber while also retaining a dose in the chamber until ready to be dispensed. An opening mechanism 30 of the device includes a cover portion 46 positioned over the opening to the dose chamber and a cutter portion 24 to break the barrier when a dose is readied for dispensing. The opening mechanism is mounted to the barrier and is movable from a first position as shown in FIG. 1*a*, where a dose is sealed within the dose chamber, to a second position as shown in FIG. 1*b* for dispensing a dose from the chamber. When in the second position, the cover and cutter portions of the opening mechanism, as shown in FIG. 1*b*, move into the air pathway to direct a portion of air to the dose chamber, as air moves through the delivery device.

Figure 1A:
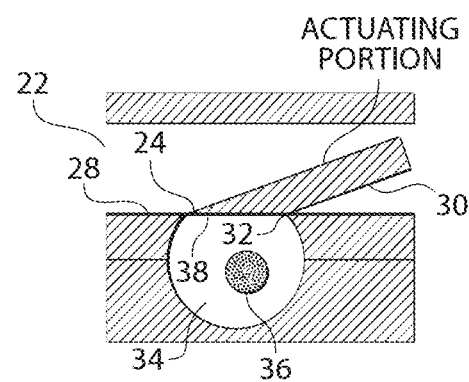
FIG. 1a shows a schematic view of a delivery device that includes a dose chamber having an opening that is sealed by a moisture barrier, and an opening mechanism positioned outside of the chamber that pivots to open the dose chamber, according to one embodiment.
Figure 1B:
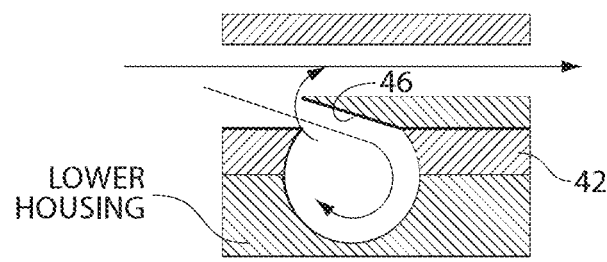
FIG. 1b shows the embodiment of FIG. 1a, with the opening mechanism in an open position.
Figure 2A:
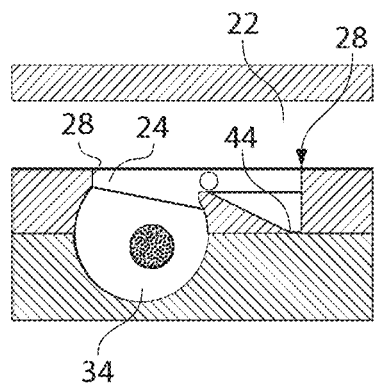
FIG. 2a shows a schematic view of a delivery device that includes a dose chamber having an opening that is sealed by a moisture barrier, and an opening mechanism with a cutter portion that is positioned on a dose chamber side of the moisture barrier.
Figure 2B:
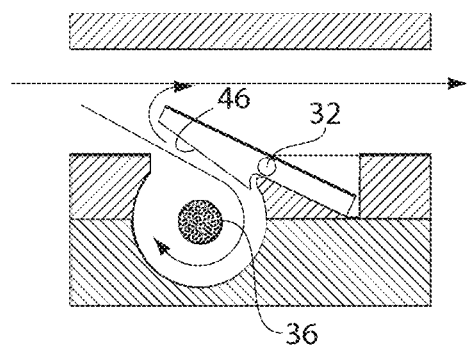
FIG. 2b shows the embodiment of FIG. 2a, with the opening mechanism in an open position.
Figure 2C:
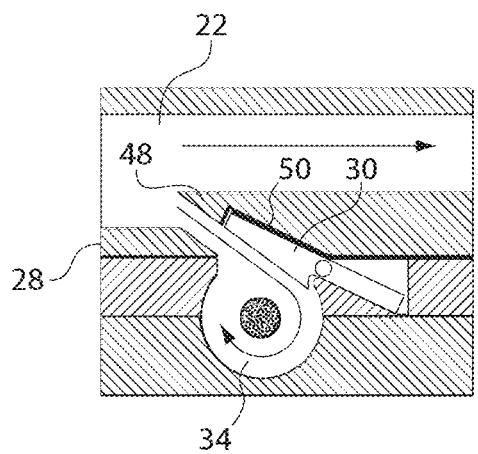
FIG. 2c shows a variation of the embodiment of FIGS. 2a and 2b that includes a stationary structure to divert air to a dose chamber, and an opening mechanism with a cutter that fits within a cavity of the stationary structure when moved to the open position, according to one embodiment.

It is to be appreciated that the general construction of the inhalation device shown in FIGS. 1*a* and 1*b* is but one embodiment and that other general constructions are also contemplated, some of which are shown in and described with respect to FIGS. 3*a*, 3*b*, 4*a*, 4*b*, 5*a*, 5*b*, 6*a*, and 6*b*. FIGS. 2*a* and 2*b* show another illustrative embodiment of a delivery device having an opening mechanism that is positioned on a dose chamber side of a barrier. As shown in FIG. 2*b*, the opening mechanism may be rotated about a pivot point 32 when an actuation region of the opening mechanism is moved to cause a cutting portion of the mechanism break the moisture barrier and to move the cover portion from the opening to provide fluid communication between the air pathway and the dose chamber. The cover portion of the cutter also moves further into the air pathway to direct air to the dose chamber, as in the embodiment of FIGS. 1*a* and 1*b*.

The embodiment of FIG. 2*c* includes some features similar to those of FIGS. 2*a* and 2*b*, but also has a stationary structure 48 that diverts air from the air pathway 22 to the dose chamber. The cutter/cover portion of the opening mechanism in the embodiment of FIG. 2*c* may be received in a cavity 50 in the stationary structure. In this embodiment, the cover and/or cutter portion of the opening mechanism may be considered to span across or cover a cavity that receives the cover/cutter. Such a configuration may allow the design of the cover/cutter and the structure that diverts air to the dose chamber to be independently optimized, although the cover/cutter may still include features that promote delivery of air to or recirculation of air through the dose chamber. For example, the structure that diverts air to the dose chamber may be substantially larger than the opening to the dose chamber, according to some embodiments. Additionally or alternatively, the diverting structure may be more easily shaped to prevent dose from traveling downstream in the air pathway 22, until drawn through the device by a subject, as is discussed herein with respect to the U-shaped air pathway in the embodiment of FIGS. 14*a*-14*c*. Various embodiments may, additionally or alternatively, include diverter like-structures, U-shaped air pathways, or other features that prevent dose from traveling in other directions, such as an upstream direction, or to prevent dose from exiting a dose chamber inadvertently. Conversely, a cutter may be optimized to cut foil or conform to the opening between the air pathway 22 and dose chamber, rather than for diverting air to a dose chamber.

The illustrative embodiment of FIGS. 3*a* and 3*b* shares many feature in to the embodiment of FIGS. 2*a* and 2*b*, but also includes a hole that extends to the dose chamber from outside of the delivery device, and that may be used to fill the dose chamber with a dose of powdered medicament or other substance. The opening mechanism, as shown, is integral with an actuator 52 that may be depressed to move the mechanism, including the cutter portion and cover portion, from the first position shown in FIG. 3*a* to the second position shown in FIG. 3*b*. Barrier layers are positioned both over the opening between the dose chamber and the air pathway, and over the filling hole and access hole to the actuator to prevent the ingress of moisture/contaminants to the dose chamber, and the egress of dose from the device. As shown, the actuating mechanism may be accessed from a side of the dose chamber that is opposite to the air pathway, a configuration that may have ergonomic advantages.

FIGS. 4*a* and 4*b* show an embodiment of a delivery device that has a lower housing that is formed of a deformable barrier material, such as a foil rather than a rigid plastic structure, to define a portion of the dose chamber. Forming the lower housing and/or other components of a delivery device out of foil or other barrier material may facilitate efficient manufacturing and/or reduce the cost to produce a delivery device. Additionally or alternatively, barrier materials may provide a dose chamber that is more resistant to moisture than dose chambers made of other materials. As shown, the lower housing includes a pivot point about which an opening mechanism, captured within the dose chamber, may rotate. The delivery device of FIGS. 4*a* and 4*b* may include an actuator that may be accessed from outside of the device to ready a dose for delivery, and/or other features of various embodiments that are discussed herein but that are not shown in FIGS. 4*a* and 4*b*.

The embodiment of FIGS. 4*a* and 4*b* includes a cavity between the positive stop 44 and actuating portion 26 of the opening mechanism, when the dose chamber is closed. This cavity is occupied by the actuation portion when the opening mechanism is moved to cut the barrier and open the dose chamber. The opening mechanism may be fit closely to the lower housing and the barrier at positions near the pivot to prevent portions of the dose from migrating to the cavity, which might otherwise prevent those portions of the dose from being delivered from the delivery device, or prevent the opening mechanism from being completely opened.

The embodiment illustrated in FIGS. 5*a* and 5*b* also has a dose chamber that is formed by a foil-on-foil structure. An opening mechanism on the dose chamber side of a barrier includes an actuating portion that may be actuated directly from outside of the chamber to move the mechanism from the first position of FIG. 5*a* to the second position of FIG. 5*b* to ready a dose for delivery. This may be accomplished by moving the actuating portion that extends from the dose chamber downward. As shown, a tab 58 of barrier or other material may be included on the mechanism to facilitate actuation.

In each of the embodiments of FIGS. 1*a*-5*b*, an opening mechanism may move through a pivoting motion when opening a dose chamber and readying a dose for delivery. By way of example, in the embodiment of FIGS. 1*a* and 1*b* the opening mechanism is adhered to an air pathway side of the barrier in a manner that creates a pivot point at the downstream edge of the opening. The opening mechanism also includes an actuation region or portion, shown extending into the air pathway 22 in FIG. 1*a*, that may be depressed to cause the mechanism to rotate about the pivot point when moving from the first position to the second position. The dose chamber side of the cover portion generally follows a rotating motion when moving from a position over the opening to a position extending partially into the air pathway 22. In embodiments that have a dose chamber formed of a barrier material, such as deformable foil that forms a lower housing in the embodiments of FIGS. 4*a*, 4*b*, 5*a*, and 5*b*, it is to be understood that the pivoting motion may accompany deformation of the lower housing and/or the upper housing, such that the pivot point may not be held in a constant position as opening mechanism is actuated. In some embodiments, the housing may include features to promote deformation in a particular manner, such as by including a crease line along a desired bend point. It is to be appreciated that other embodiments may include opening mechanism that ready a dose for delivery through other motions, such as by translation or through combinations of rotation and translation, as is discussed in greater detail herein, and that the embodiment of FIGS. 1*a* and 1*b* is not to be considered limiting in this respect.

Figure 3A:
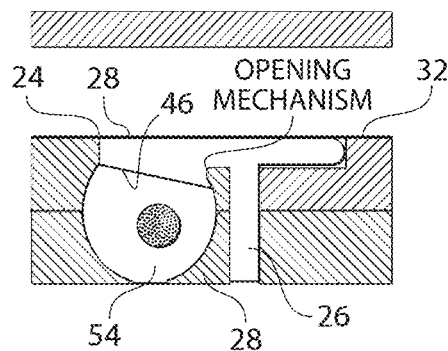
FIG. 3a shows a schematic view of a delivery device that includes a filling hole that provides access to the dose chamber and that is sealed by a barrier and an actuator that is accessible from a bottom surface of the device, according to one embodiment.
Figure 3B:
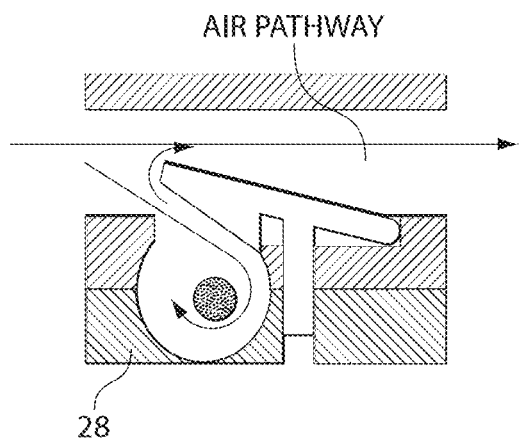
FIG. 3b shows the embodiment of FIG. 3a, in configured for delivery a dose.
Figure 4A:
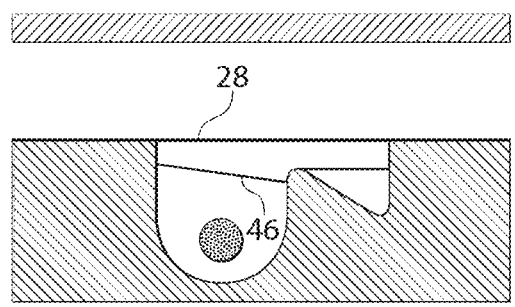
FIG. 4a shows a schematic view of a delivery device that includes a dose chamber formed of barrier material, and a cutter that is positioned inside of the dose chamber.
Figure 4B:
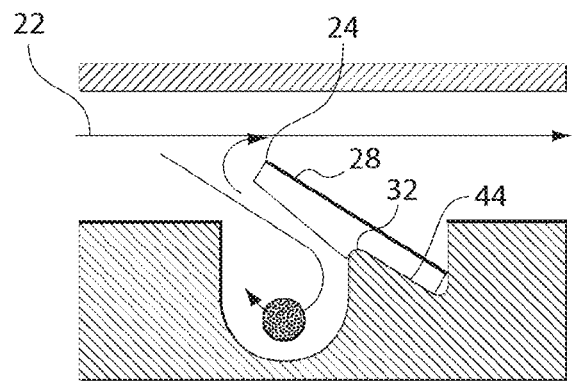
FIG. 4b shows the embodiment of FIG. 4a, with the opening mechanism in an open position.
Figure 5A:
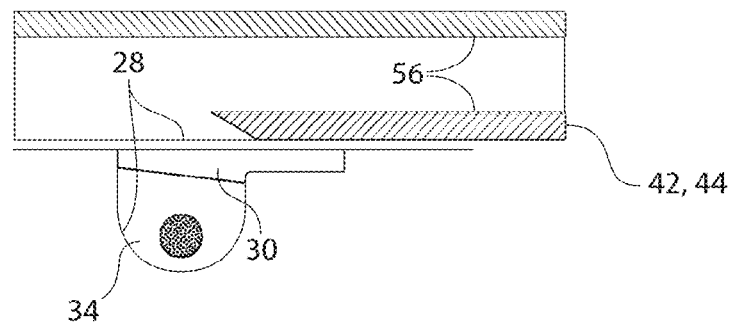
FIG. 5a shows a schematic view of a delivery device that includes a dose chamber formed of barrier material and having an opening mechanism positioned inside of the chamber that may be actuated directly from outside of the chamber.
Figure 5B:
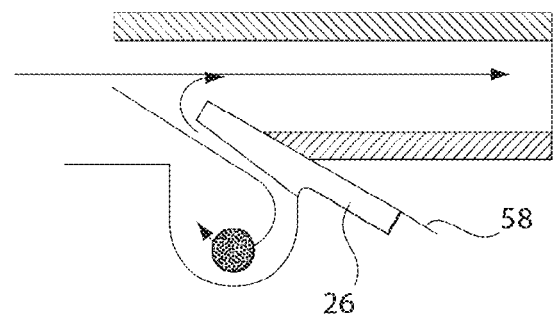
FIG. 5b shows the embodiment of FIG. 5a, with the opening mechanism in an open position.
Figure 6A:
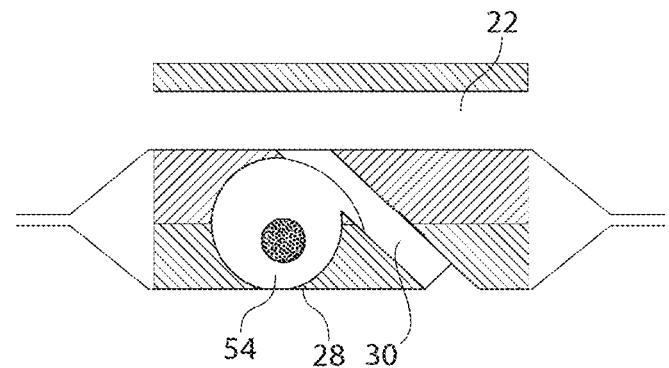
FIG. 6a shows a schematic view of a delivery device that includes an opening mechanism that translates from a first position to a second position to ready a dose for delivery.
Figure 6B:
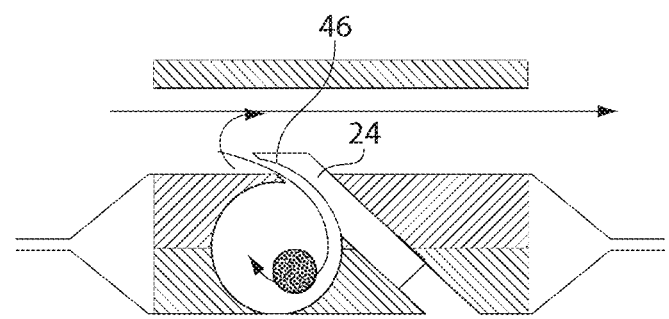
FIG. 6b shows the embodiment of FIG. 6a, with the opening mechanism in the second position.

FIGS. 6*a* and 6*b* show one embodiment of a delivery device in each of a first and second position, respectively, and that has an opening mechanism that translates, rather than pivots. The dose chamber is formed between an upper and lower housing, and includes a fill opening 54, as in the embodiment of FIGS. 3*a* and 3*b*. A foil-on-foil cover surrounds the entire dose chamber and opening mechanism to provide a light, moisture, and/or contaminant barrier for any dose contained therein. To ready a dose for delivery, a user moves the opening mechanism from the position shown in FIG. 6*a* to the position shown in 6*b*, either by moving an actuator (not shown) that acts on the mechanism, or by pressing on the mechanism directly. This causes the mechanism to translate, pressing a cutter portion of the mechanism into and shearing the barrier while moving a cover portion away from the opening. The cutter portion/cover portion then moves into the air pathway to a position where air flow will be diverted to the dose chamber, as is described in greater detail herein with respect to various embodiments. In other embodiments, opening mechanisms may translate in other directions, relative to a dose chamber to open fluid communication to an air pathway 22, or may translate in combination with rotating, as aspects of the invention are not limited in this respect.

Figure 7A:
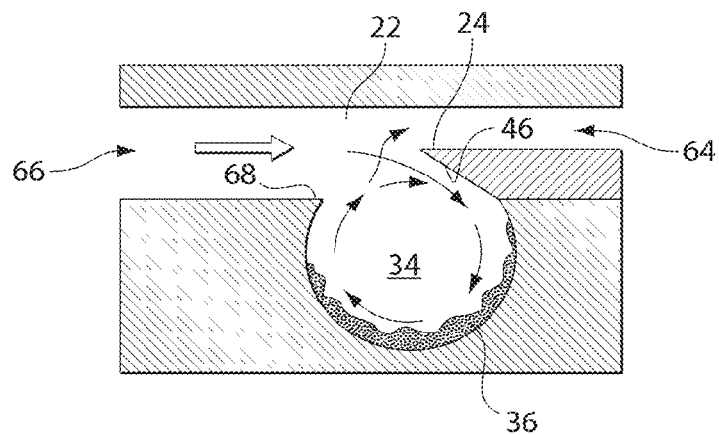
FIG. 7a shows a side view of air flow through the air pathway and dose chamber of a delivery device during delivery of a powdered medicament, according to one embodiment.

Once a dose is readied for delivery by actuating an opening mechanism, air is moved through the pathway either by being drawn or pushed through the delivery device, actively or passively, to entrain the dose from the chamber and deliver the dose to a subject. As shown in FIG. 7*a*, which is a schematic side view of air flow through the embodiment of FIGS. 1*a* and 1*b*, air moves from an upstream portion of an air pathway toward a downstream portion 64. The cover portion, when in an open position, is positioned at least partially in the air pathway to direct a portion of the air moving through the pathway to the dose chamber. In the illustrated embodiment, air that enters the dose chamber progresses along the dose chamber side of the cover portion and then follows the substantially curved interior wall of the dose chamber until the air flow is directed back towards the opening and/or the dose chamber side of the cover. A portion of the air that is directed back toward the cover of the dose chamber may be recirculated back through the dose chamber by air that is entering the dose chamber, or by the cover itself. Another portion of the air, however, exits the dose chamber to re-enter the air pathway and move downstream to deliver dose, entrained from the chamber, to the downstream portion of the air pathway and eventually to a subject. It is to be appreciated that although air and/or dose recirculation may occur in the embodiment of FIGS. 1*a* and 1*b*, such recirculation may not occur in other embodiments. By way of example, according to some embodiments, a chamber may be opened to allow air to enter and then directly pass through a chamber, as dose is entrained.

Recirculation of air through the chamber, as described above, may promote an even metering of dose from the dose chamber by preventing an entire dose, or a substantial portion of a dose, from exiting the chamber as a bolus or clump of powder. Additionally or alternatively, recirculation may promote the retention and break up of any larger agglomerated particles prior to being delivered from the dose chamber. This may occur as entrained particles tumble about the chamber and are broken down into smaller particles for improved delivery. Additionally, larger particles entrained within the flow may have too much momentum to turn back toward the opening, as the flow of air turns toward the air pathway to exit the chamber. These larger particles may continue on a path toward the dose chamber side of the cutter or cover and become entrained in the flow of air that is entering the chamber. In this respect, the larger particles may be recirculated back through the chamber, at least longer so than smaller particles, to be de-agglomerated into smaller particles prior to delivery. Particles over a threshold size may be retained within the dose chamber indefinitely, according to some embodiments.

Figure 7B:
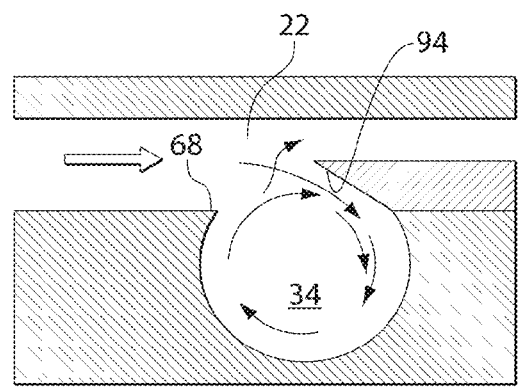
FIGS. 7b and 7c show delivery devices having openings between a dose chamber and air pathway configured to alter flow properties, according to some embodiments.
Figure 7C:
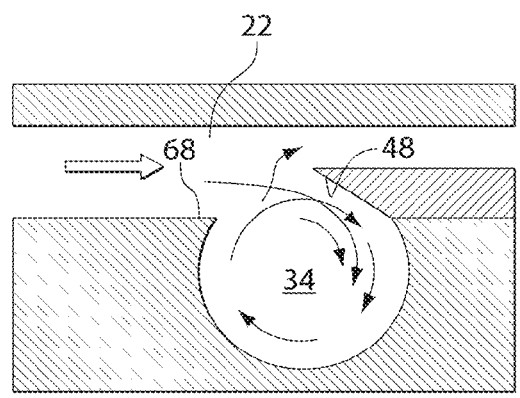

The shape of size or the opening between a dose chamber and air pathway may be altered to, in turn, alter recirculation characteristics or other flow characteristics of a delivery device. By way of example, FIG. 7*b* shows another embodiment that has an opening with an upstream edge that is positioned further downstream than in the embodiment of FIG. 7*a*. This reduces the size of the opening, which causes flow to recirculate longer within the dose chamber. The wall of the dose chamber in FIG. 7*b* is also angled to direct flow more toward an inside portion of the opening, and less toward the air pathway, at least with respect to the embodiment of FIG. 7*a*, which also causes dose to recirculate within the chamber to a greater degree than in the embodiment of FIG. 7*a*. The embodiment FIG. 7*c* includes an opening that has overlapped upstream and downstream edges, which further increases the amount of recirculation that occurs within a dose chamber. It is to be appreciated that other factors may be altered as well to modify flow and recirculation characteristics through a dose chamber. For instance, in some embodiments, the opening between the dose chamber and air pathway may have a smaller width (that is, the direction into/out of the page in FIGS. 7*a*-7*c*) than the dose chamber and/or the air pathway. Decreasing the width of the opening, all else constant, will generally increase the amount of dose recirculation that occurs within a dose chamber.

The curved shaped of the dose chamber, according to some embodiments, may also help promote metered delivery of dose from a delivery device. As shown in FIG. 7*a*, dose may also be pushed outwardly against the interior wall of the dose chamber as air circulates about the chamber. Air that then flows across the surface of the medicament may entrain particles of the medicament, in a metered manner, as the flow progresses about the dose chamber. As shown, the interior surface of the chamber substantially lacks sharp corners or pockets that might otherwise trap portions of a dose and prevent them from being delivered, or from being delivered in a metered manner. It is to be appreciated, however, that other embodiments may include sharp corners or pockets that are intentionally placed to trap or retain portions of a dose, as retaining a portion of dose for a longer time period may be desirable in some embodiments.

The amount of recirculation that occurs in a dose chamber and/or the rate at which dose is metered from a chamber by air flowing therethrough may be controlled by the shape of a dose chamber and/or cover portion of a delivery device. By way of example, decreasing the size of the opening between the air pathway and dose chamber may result in slower metering of dose from the chamber, generally speaking. Additionally, orienting the surfaces of the dose chamber to direct flow more toward the cover portion or other surfaces of the dose chamber, rather than out of the chamber through the opening, may result in a greater amount of recirculation and/or mixing within the chamber, and a slower rate of dose metering from the chamber. In this respect, it is to be appreciated that although the dose chambers are illustrated as having primarily cylindrical cross-sectional shapes, that other configurations are possible, including elliptical shapes, shapes having complex curvatures, or even more simplistic shapes, such as rectangular or partially rectangular, as aspects of the invention are not limited in this respect. Additionally or alternatively, openings between the air pathway and dose chamber may be altered to, in turn, alter the rate at which dose is metered from a dose chamber.

Figure 8:
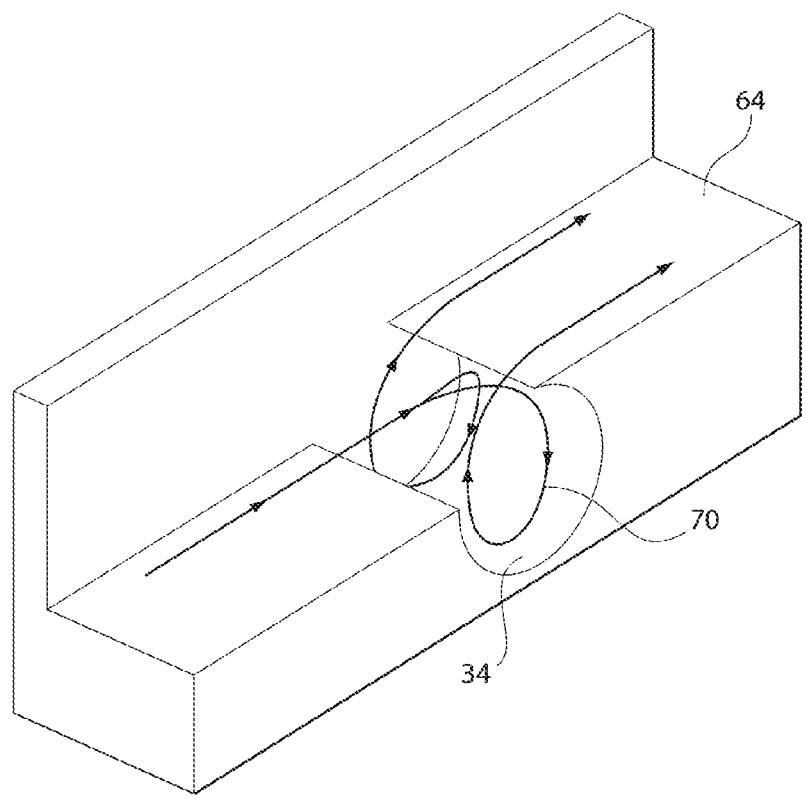
FIG. 8 shows a perspective cutaway view of air flow through the air pathway and dose chamber of a delivery device, according to one embodiment.

FIG. 8 shows the flow of air through an air pathway and dose chamber from a perspective top view, as may occur in the embodiment of FIGS. 1-6. As represented by the arrows, air nearer to central portions of the air pathway typically travels at greater velocities than air nearer to lateral side walls of the air pathway, due to boundary effects at the walls. The air that is moving faster toward the opening of the dose chamber may naturally provide a pathway for air to enter a dose chamber, as shown in FIG. 8. As is to be appreciated by those of skill in the art, the amount of air entering a dose chamber is equal to the amount of air that exits the dose chamber, at least at steady state. Given this, portions of the air pathway in which air is moving downstream more slowly, such as near lateral walls 72 of the air pathway, may provide less resistance against flow that is working back to the pathway from the dose chamber. FIG. 8 shows how air entering the chamber at a central portion of the opening may travel in a corkscrew-like manner in each lateral direction and about the substantially cylindrical surface of the dose chamber as the flow circulates about the chamber back towards the air pathway 22, near lateral portions of the opening. Interactions and or cross-flows between air that is entering and exiting the chamber at the opening and interacting at other positions along the corkscrew-like path may promote dispersion and/or de-agglomeration of powdered medicament that is being delivered by the delivery device.

Figure 9:
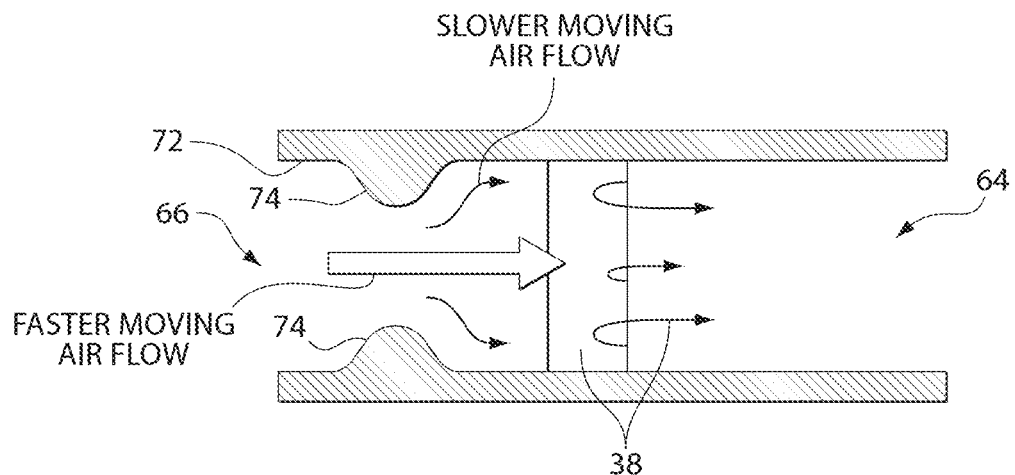
FIG. 9 shows a delivery device that includes a restriction in the air pathway, upstream of an opening to a dose chamber, according to one embodiment.

According to some embodiments, inhalation devices may include features to promote a particular shape of flow through a dose chamber, such as the corkscrew-like path shown in FIG. 8, or other chaotic, eddying paths. By way of example, the embodiment of FIG. 9 incorporates bumps 74 positioned on each lateral wall of the air pathway 22, upstream of the opening to the dose chamber. The bumps create a restriction at a central portion of the air pathway that causes air flowing therethrough to increase in velocity, while flow at areas near the lateral walls downstream of the restriction is slowed. Increasing and slowing flow through the air pathway in this manner may create a more pronounced corkscrew-like flow path through the chamber that may, in turn, increase turbulence and mixing of dose in a delivery device. It is to be appreciated that the restriction shown in FIG. 9 is but one configuration that may be used to promote a particular shape of flow through a dose chamber, and that others are also possible. One embodiment may be constructed like that shown in FIG. 9, but with only a single bump forming a restriction. Here, flow velocity may be increased along the wall that lies opposite to the bump, while being slowed downstream at the wall having the bump. Altering flow in this manner may promote a flow shaped to have a single corkscrew-like path that leads from one lateral side of a cylindrical chamber to the opposite lateral side. Other configurations are also possible, including arrangements that have a plurality of bumps or other features extending into the flow pathway to increase and/or decrease flow rates at a plurality of regions and cause a greater amount of turbulence at the opening of a dose chamber or inside of a dose chamber.

Figure 10:
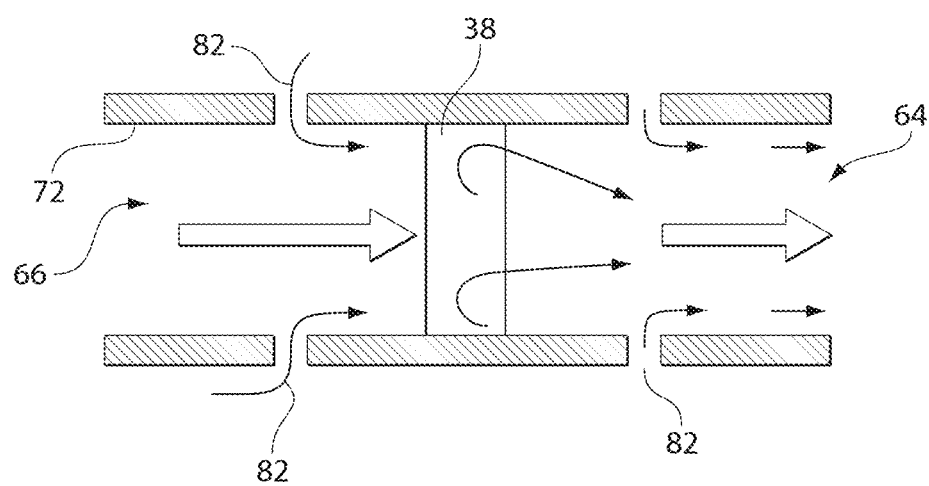
FIG. 10 shows a delivery device that includes a first set of vents that lead into the air pathway, upstream of an opening to a dose chamber, and a second set of vents that lead into the air pathway, downstream of the opening, according to one embodiment.

According to some embodiments, vents 82 may be incorporated into an inhalation device to help form a particular shape of flow through the device. As shown in FIG. 10, vents may be positioned in the air pathway, upstream of the opening to the dose chamber. As air is moved through the air pathway from the upstream portion 66 towards the downstream portion, air is also drawn into the pathway through the vents. The vents may be sized such that air passing through the vents moves at a slower rate than air moving through the air pathway from an upstream portion. Flow in this manner can create an effect similar to that of the restriction discussed above with respect to FIG. 9. Air traveling through central portions of the pathway from the upstream portion moves at a greater velocity than air traveling at lateral portions of the pathway, which can produce a corkscrew-like pattern, similar to that discussed above with respect to FIGS. 8 and 9. According to some embodiments, vents may be angled to direct flow in a particular manner as the air enters the pathway.

Vents may be incorporated into a delivery device at other positions as well. By way of example, the embodiment of FIG. 10 also includes vents that lead into the air pathway at a position downstream of the opening. Air that enters the pathway through these vents may cause further turbulence in the downstream pathway to provide additional mixing of dose that is delivered from the chamber. Additionally or alternatively, the vents, when positioned circumferentially about the downstream portion, may provide an annular shaped cushion of air about the flow of air that contains an entrained dose. Having such an annular shaped cushion may prove beneficial in keeping the dose away from the walls of the air pathway and/or walls of a subject's throat during delivery to the subject's lungs.

Figure 11:
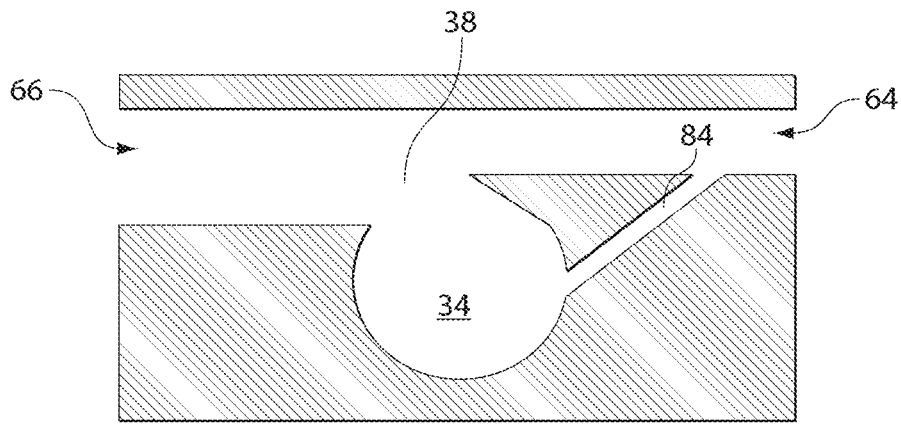
FIG. 11 shows a delivery device that include a bypass between a dose chamber and downstream portion of an air pathway, according to one embodiment.

According to some embodiments, a bypass 84 may be incorporated into a delivery device between a dose chamber and a downstream portion of an air pathway 22, as shown in the embodiment of FIG. 11. The bypass may allow some of the pressure in the dose chamber to be released to the downstream portion of the air pathway, without necessarily allowing dose to be dispensed through the bypass. Reducing the air pressure level, in this manner, may allow more air to enter the dose chamber to better mix and/or entrain medicament, and/or allow dose to be metered from the chamber at an increased rate. The cross-sectional size of the bypass, relative to the size of the opening to the dose chamber, may be adjusted to provide different degrees of bypass. Additionally or alternatively, the bypass may be shaped and/or may include features, such as a screen, to prevent dose from being delivered downstream, through the bypass. It is to be appreciated, however, that in other embodiments, some dose delivery through the bypass may be desirable, and that the bypass may be shaped and sized to promote the passage of dose therethrough. It is also to be appreciated that, according to some embodiments, two or more bypasses may be included in a delivery device, as aspects of the invention are not limited to that shown in the figures.

Figure 12:
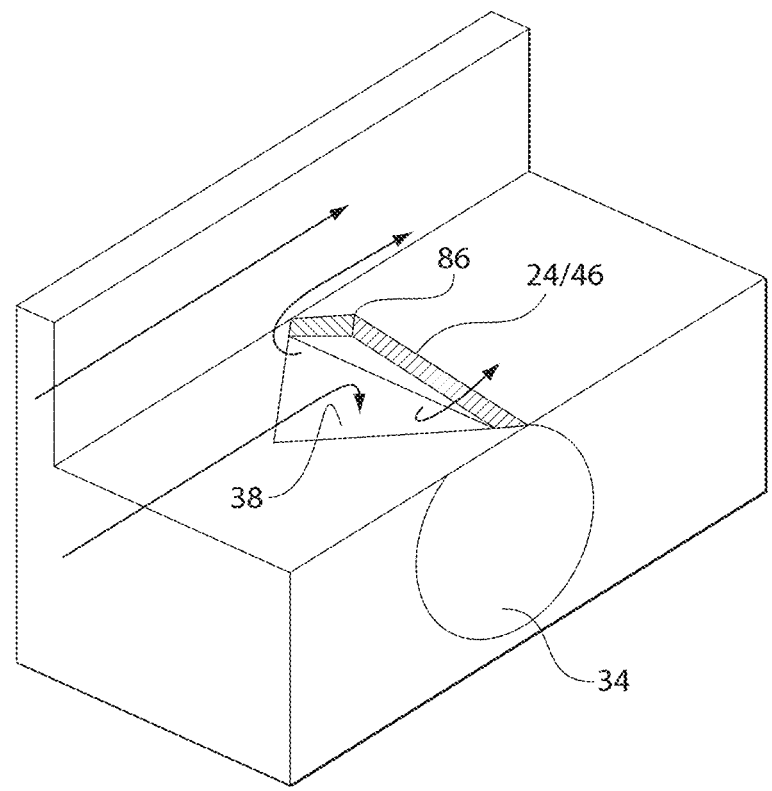
FIG. 12 shows a cover portion of an opening mechanism that is substantially triangle shaped, according to one embodiment.

The cover portion/cutter portion of the opening mechanism may extend into the air pathway when the delivery device is readied for dose delivery, and may be shaped to accomplish different effects. By way of example, according the embodiment shown in FIG. 12 the portion of the cover that extends to the pathway may be shaped substantially like a triangle, extending to a point 86 in the pathway and overlying a substantially triangular opening to a dose chamber. In such an embodiment, the pointed end of the cover may divert faster flowing air 76 from the central area of the air pathway, while also providing greater room at lateral areas of the pathway and opening for air to escape from the dose chamber. Additionally or alternatively, the reduced area of the triangle point may create greater pressure against a barrier, when the opening mechanism is actuated to open a dose chamber. It is also to be appreciated, however, that the cover may have a different shape than the opening, according to some embodiments. For example, in one embodiment a triangular shaped cover may overhang an opening having a square shape.

Figure 13:
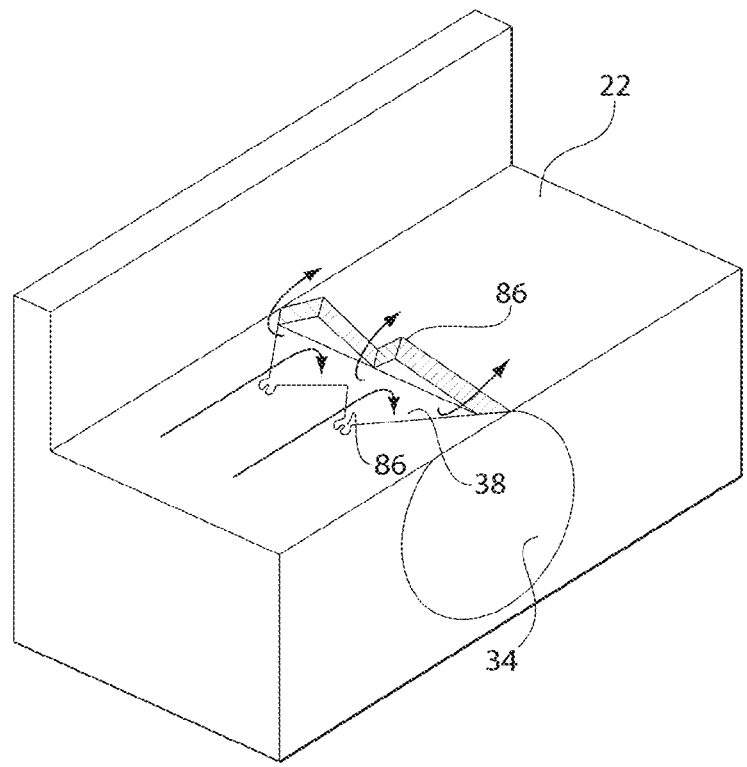
FIG. 13 shows a cover portion of an opening mechanism that includes a pair of substantially triangle shaped portions, according to one embodiment.

The cover portion embodiment of FIG. 13 includes a pair of points that extend into the air pathway when the dose chamber is open. The pair of points creates two primary areas in which air enters the dose chamber from the pathway. In this embodiment, air typically will exit the chamber near the lateral walls of the air pathway and often in the area between each of the points. A cover configured in this manner may create corkscrew-like paths extending in each lateral direction away from areas under each point as air flows through the dose chamber. This may increase the amount of turbulence in the device, enhancing dose mixing and de-agglomeration during delivery. As in the embodiment of FIG. 12, the points of the cover shown in FIG. 13 may also help to create high pressure areas when a barrier is opened. It is to be appreciated that cutter portions may have different shapes, such as square, curved, circular, and more complex shapes, and that the shapes of FIGS. 12 and 13, are merely examples associated with two embodiments.

In each of the embodiments of FIGS. 12 and 13, the cutter portion of the opening mechanism includes one or more points that may help concentrate forces to a high pressure point when opening a barrier that covers a dose chamber opening. It is to be appreciated that other features may also be used to concentrate forces. By way of example, according to some embodiments, a cutter portion may include a raised point or edge to concentrate forces against a barrier. The raised point or edge of the cutter may be formed by a slight bend in the opening mechanism, deformation of the opening mechanism, or by a localized portion of the cutter portion that is raised relative to adjacent portions. In other embodiments, a sharp point or other type of energy directing features may be incorporated into a side wall of an air pathway or directly into a structure that overlies the barrier about the perimeter of an opening. The point may be contacted to break a barrier when the barrier is urged upward by an opening mechanism. Other features may additionally or alternatively be incorporated into a delivery device, such as pre-scored barriers, and the like, as the examples shown in FIGS. 12 and 13 and discussed above are merely exemplary.

Various embodiments may also include features that allow a barrier to be readily punctured. By way of example, the opening shown in FIG. 13 includes a pointed structure that lies opposite to a pointed structure on the cover. These opposed, pointed structures interact to concentrate forces in a small area on the barrier that lies therebetween when the opening mechanism is actuated. This may result in a high pressure on the barrier that promotes rupture and then tearing of a barrier. It is to be appreciated that the opposed points shown in FIG. 13 are but one configuration of features that may help concentrate forces to promote breakage of a barrier, and that others are also contemplated.

It may be desirable to prevent a barrier from being sheared in a way that creates jagged and/or inconsistently sheared edges which might otherwise extend into an air pathway and disrupt flow through a delivery device in an unpredictable manner or create catch points for dose that is being delivered. According to some embodiments, the cutter portion of the opening mechanism and/or an edge of opening itself may include features to promote a clean and consistent rupturing of the barrier when the dose chamber is opened. By way of example, in each of the embodiments of FIGS. 12 and 13, the upstream edge 68 of the cover and the opening are formed to have a similar shape (except for the rounded areas near the points of the opening, discussed above with respect to FIG. 13) and to lie adjacent to one another when the dose chamber is closed. In this manner, the line that lies between the upstream edge of the cover and the opening define a line along which the barrier will be sheared, consistently, when opened. Other features may, additionally or alternatively, be incorporated into a device to promote consistent barrier shearing. For example, barriers may be weakened along a desired shear line, such as by scoring, to promote barrier rupture in a particular manner.

According to some embodiments, a barrier may be sandwiched between a pair of rigid structures near all or a portion of a perimeter about an opening, such as is shown in FIG. 2*c*. Sandwiching the barrier, in this manner, may promote clean and consistent rupture of the barrier when opened, particularly where the forces associated with rupturing a barrier might be great enough to overcome the forces that keep the barrier adhered to the perimeter of the opening, the cover portion/cutter portion, or other structure of a delivery device. Points or energy directors, like those discussed herein, may be incorporated into one or both structures that sandwich a barrier, according to some embodiments.

The cover portion of the opening mechanism may be shaped to completely block the opening to the dose chamber when in the closed position to prevent the escape of dose from the chamber and/or the ingress of contaminants, including moisture, as in the embodiments of FIGS. 1-6. According to some embodiments, however, the cover alone may seal a dose chamber, such that a barrier may be omitted from the inhalation device altogether. Additionally or alternatively, the cover may be larger than the opening, which according to some embodiments, may provide a diverting structure that extends further or that includes a larger surface area. It also is to be appreciated that in other embodiments, however, the covering portion may only occupy a portion of the opening when the dose chamber is closed, and that sealing may be accomplished primarily or solely with a barrier.

The barrier that is incorporated into some embodiments may be formed of various materials. According to some embodiments, the barrier includes an aluminum foil that is substantially impervious to light and moisture, although in other embodiments, barriers may be permeable to some degree of moisture and light. The barrier may be readily adhered to other barriers, such as for foil-on-foil embodiments described herein, or to other structures of a delivery device, that are often formed of plastic. Adhesives, heat weld, friction welds, and other fastening techniques may be used to affix barriers and to provide a seal between the barrier and mating structure.

According to some embodiments, the cover may be constructed to move consistently to the same open position, which may help promote consistent delivery of air to the dose chamber and of dose from the dose chamber. A positive stop may be incorporated in the device that, when reached, prevents an opening mechanism and cover portion from opening further. By way of example, the cover in the embodiment of FIGS. 1*a* and 1*b* is prevented from opening further when the opening mechanism abuts the air pathway 22, as shown in FIG. 1*b*. The embodiment shown in FIG. 2*a* also includes a positive stop in a cavity at the bottom of the air pathway that receives the actuating portion of the opening mechanism and that prevents further movement of the cover when abutted by the opening mechanism. Additionally or alternatively, the opening mechanism may be shaped to have a slight interference fit with the air pathway 22, or other portions of the delivery device, which may help hold the cover/opening mechanism in the open position. According to some embodiments, the edges of the cutting or covering portions may be spaced slightly from the walls of the air pathway to allow edges of a sheared barrier to be wiped by the passing of the opening mechanism, and moved out of the airflow pathway.

Delivery devices may include features to retain the position of a pivot point of an opening mechanism during and/or after the opening of a dose chamber. In the embodiment of FIGS. 1a and 1b, the opening mechanism is held relative to the air pathway by the barrier. Here, the barrier acts as a living hinge to hold the pivot point steady when and after the cover is opened. Similarly, in the embodiment of FIGS. 2a and 2b, the opening mechanism is held to the delivery device by a pin joint that acts as a pivot. In other embodiments like those of FIGS. 4a, 4b, 5a, and 5b, portions of the barrier that are attached to both the opening mechanism and the air pathway remain intact as the cover moves to the open position. These portions help keep the pivot point between the cover and the air pathway in a common position both during and after the dose chamber is opened.

Although not shown in all of the drawings, each of the embodiments of FIGS. 1-6, may include a plunger or other type actuator that may be actuated by a user to move an opening mechanism from a first position, where a dose chamber is closed, to a second position, where the dose chamber is opened to ready a dose for delivery. By way of example, a plunger may extend downwardly and through the air pathway to press on the actuation portion of the opening mechanism in either of the embodiments shown in FIGS. 1a, 1b, 2a, and 2b. Various mechanisms may be used to move the plunger downward and/or to return the plunger from the air pathway 22, once a dose has been readied for delivery. One non-limiting example of such a mechanism includes a plunger that may extend, when actuated, from an upper surface of the delivery device shown in either of the embodiments of FIGS. 1a, 1b, 2a, and 2b, directly above an actuating portion of the opening mechanism. A spring or other biasing element may be incorporated into the inhalation device to move the plunger away from the opening mechanism, after actuation.

Figure 14A:
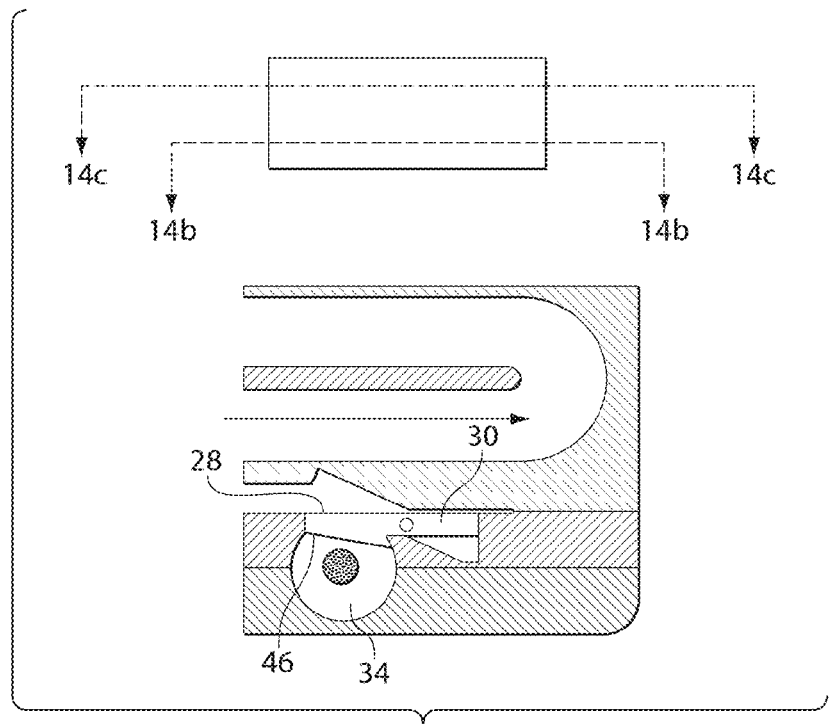
FIGS. 14a-14c show a delivery device that includes separate inlet and outlet regions of an opening between an air pathway and a dose chamber, an air inlet channel and an air outlet channel that lead to an opening of a dose chamber, and a primary air path that has a U-shaped structure, according to one embodiment.
Figure 14B:
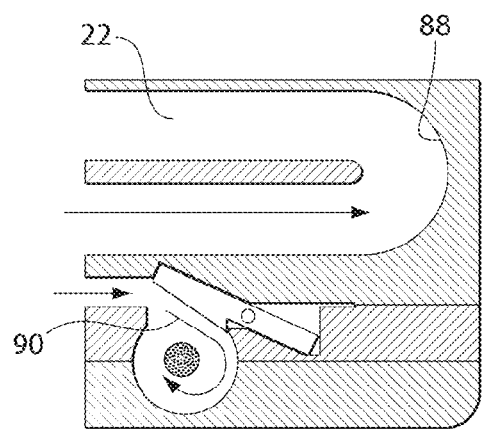
Figure 14C:
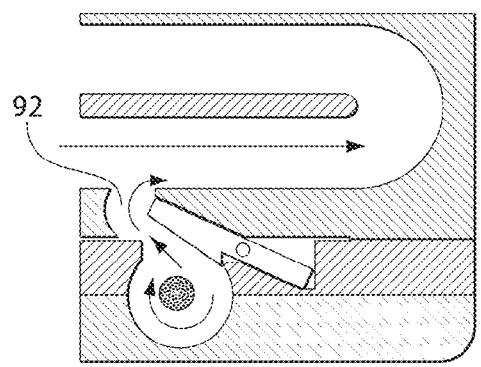

It is to be appreciated that the embodiments of FIGS. 1-6 and the variations thereof, as discussed above, are non-limiting examples of the types of delivery devices that may incorporate the various inventions described herein, and the inventions may additionally or alternatively be incorporated into different embodiments. FIGS. 14a-14c show yet another embodiment of a delivery device that incorporates various aspects of the inventions discussed herein with respect to other embodiments. As shown, the device includes a lower housing that mates with an upper housing to define a dose chamber therebetween. The device has a primary air pathway 118 that includes a U-shaped downstream portion. A chamber inlet pathway, separate from the primary air pathway 22, provides an inlet to the dose chamber. A chamber outlet pathway connects the dose chamber to the primary air pathway 22. A barrier, such as a foil, is sandwiched between the upper and lower housings to seal an opening of the dose chamber and to retain and protect a dose of medicament in the chamber until ready to be dispensed. An opening mechanism is also sandwiched between the upper and lower housings. As in other embodiments discussed herein, the opening mechanism includes a cutter portion positioned inside of the chamber and that may move or pivot from a first position, for storing a dose, to a second position to break the barrier at the opening of the dose chamber, placing the dose chamber in fluid communication with the primary air pathway through each of the inlet and outlet pathways.

As may be seen in FIG. 14b, the opening mechanism may be received in a cavity in the air inlet 90 and outlet 92 channels to direct flow to the dose chamber, rather than extending into a primary air pathway, as in other embodiments described herein. In this respect, the cover and/or cutter portion of the opening mechanism may fit within a larger structure that diverts air toward a dose chamber, and may be considered to span across or cover a cavity that receives the cover/cutter.

As shown in FIGS. 14b and 14c, the inlet and outlet pathways are in fluid communication with the dose chamber at laterally separate portions of the chamber. That is, discrete inlets and outlets to the chamber are defined by structures of the device, unlike in some other embodiments. These discrete inlets and outlets may be positioned to cause flow to corkscrew 70 through the dose chamber from one lateral end to the other lateral end as the flow moves from the primary air pathway, through the inlet pathway, dose chamber, and then outlet pathway. Alternatively, the discrete inlet(s) and outlet (s) may be positioned to allow air to pass directly through the chamber, entraining dose without substantial recirculation or corkscrewing, as aspects of the invention are not limited in this respect. It is also to be appreciated that the device shown in FIGS. 14a-14c, or variants thereof, may be used without a primary air pathway. That is, air may flow directly to the air chamber through an air inlet pathway, and then directly to a subject, through an outlet pathway, such that substantially all of the air that enters the device, passes through the dose chamber.

Figure 15:
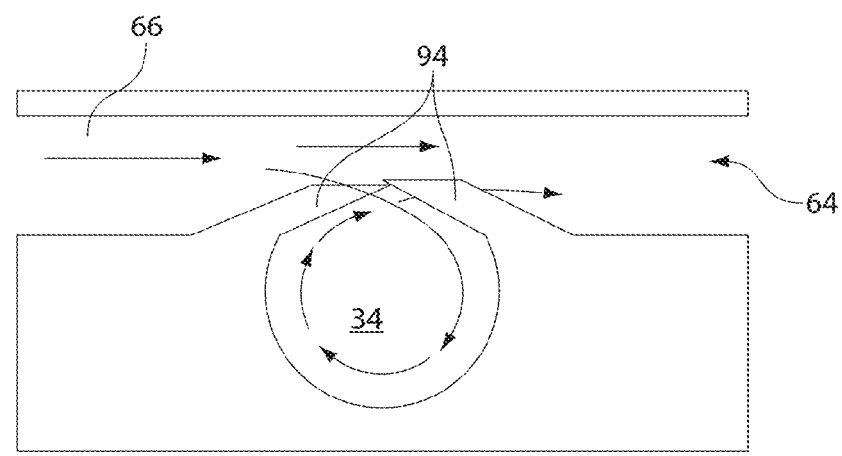
FIG. 15 shows a schematic view of a delivery device that includes diverters facing both upstream and downstream in an air pathway, according to one embodiment.

FIG. 15 shows yet another embodiment of a delivery device that may be used to meter the delivery of a dose to a subject. As shown, the device includes covering portions or diverters 94 that face both in the upstream direction and the downstream direction of the primary air pathway. Each diverter is positioned at a laterally separate portion of the opening to the dose chamber to define an entrance and exit from the dose chamber, as in the embodiment of FIGS. 14a-14c. Air flow may enter the dose chamber in a manner similar to that discussed herein with respect to the embodiments of FIGS. 1-6. However, the diverter that faces downstream substantially reduces resistance to outlet flow from the dose chamber. This may result in substantially less circulation of flow in the dose chamber and a more rapid delivery of a dose therefrom, which may be desirable for some applications. It is to be appreciated that although the diverters shown in FIG. 15 are constructed similarly (except for facing different directions) that other embodiments may have diverters constructed differently, such as by having different widths, heights, or general shapes. It is also to be appreciated that each of the diverters shown in the embodiment of FIG. 15 may act as opening mechanisms that, when operated, rupture a barrier to or from the dose chamber to provide access thereto. Other embodiments may, additionally or alternatively, include multiple cutters/covers, as aspects of the invention are not limited in this respect.

It is to be appreciated that although various embodiments of the delivery devices are discussed and illustrated herein as single dose device, that a plurality of any of the delivery devices may be incorporated into a device that may deliver multiple doses. Incorporating multiple dose chambers into a common device may allow some features of a delivery device to be shared among different dose chambers. By way of example, a multi-dose device may include a common outlet that is used to deliver, sequentially, doses from each of the dose chambers to a subject, when needed. Other features may be shared among the different dose chambers of a common, multi-dose device, such as a single actuator/plunger that is moved sequentially into registration with each dose chamber to move an opening mechanism between a first and second position to ready a dose for delivery.

Figure 16A:
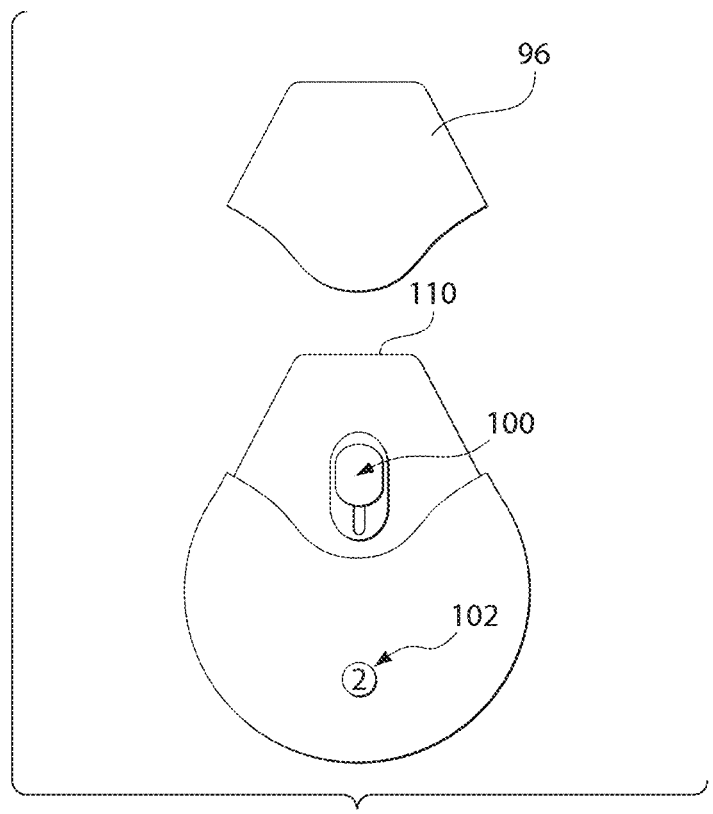
FIGS. 16a-16c show one illustrative embodiment of a multi-dose device.
Figure 16B:
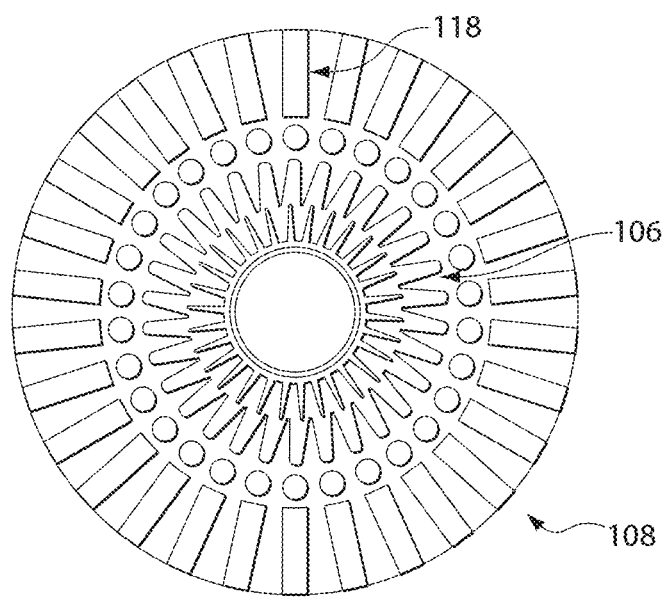
Figure 16C:
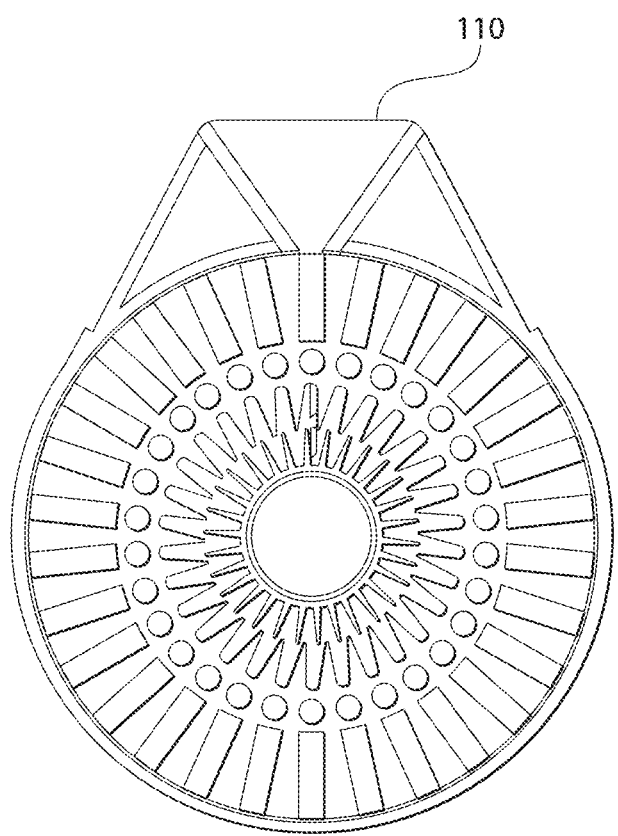

FIGS. 16a-16c illustrate one embodiment of a multi-dose device that incorporates the delivery device described herein with respect to FIGS. 14a-14c. FIG. 16a shows an external view of the device, including an outer housing 98 that has an outlet 110 shaped to be received by the mouth of a subject and that may be placed, sequentially, in fluid communication with the air pathways of each delivery device when a dose is readied for delivery. The device also includes a button 100 that may be actuated to move delivery devices inside of the device sequentially into registration with the outlet to ready a dose for delivery and/or to move an actuator to open a dose chamber, as discussed herein. The housing also includes a window through which a dose counter 102 may be viewed so that a user may be aware of the number or doses that have been expended or the number of doses that remain. A cover 96, also shown in FIG. 16*a*, may be positioned over the outlet, when the device is not in use.

FIG. 16*b* shows a disc 108 that incorporates a plurality of dose chamber and air path pairs, or "dispersion engines" as alternately referred to herein. The disc may be received into the housing of FIG. 16*a*, as shown in the cross-sectional view of FIG. 16*c*. Each of the dispersion engines are oriented with the outlet of the air pathway facing toward the outer edge of the disc for alignment with the outlet of the multi-dose device. Each dispersion engine also includes an interface that mates with the button or other actuator of the multi-dose device to facilitate movement of an opening mechanism that may open a dose chamber to ready a dose for delivery. The disc also includes indexing features 106 that may be engaged when the button is actuated to sequentially move different dispersion engines into alignment with the outlet.

Figure 17A:
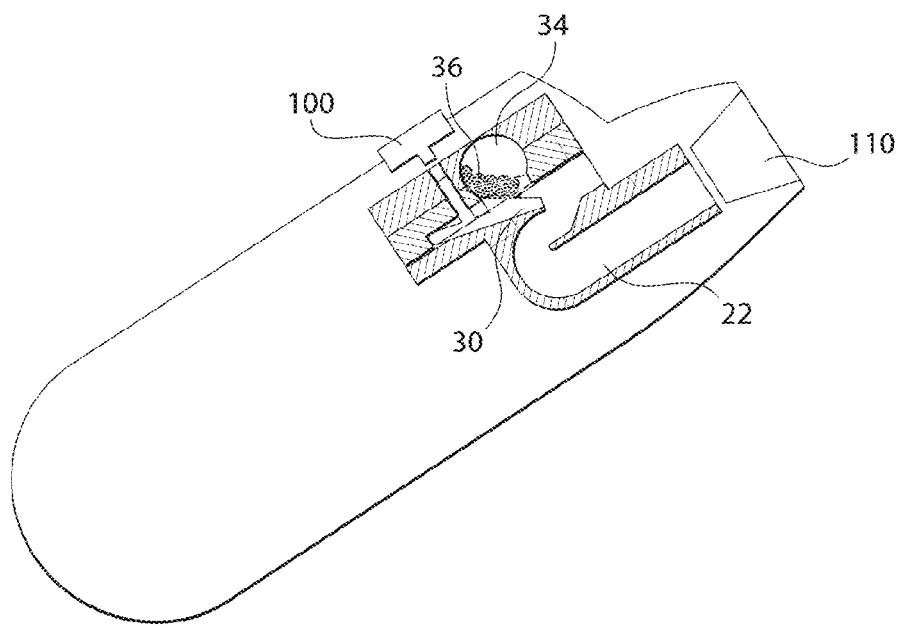
FIGS. 17a-17c show the position of a dose within a delivery device as the device is opened, and moved to as subject's mouth for delivery.
Figure 17B:
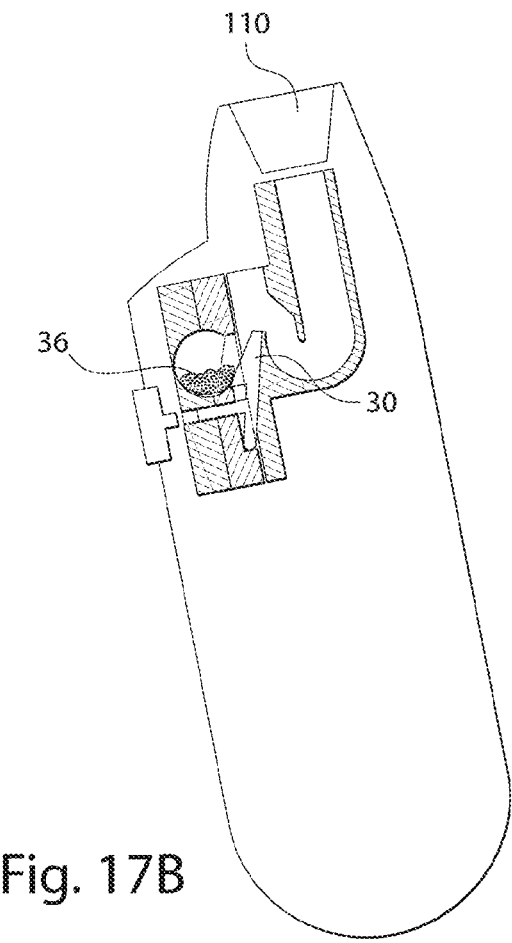
Figure 17C:
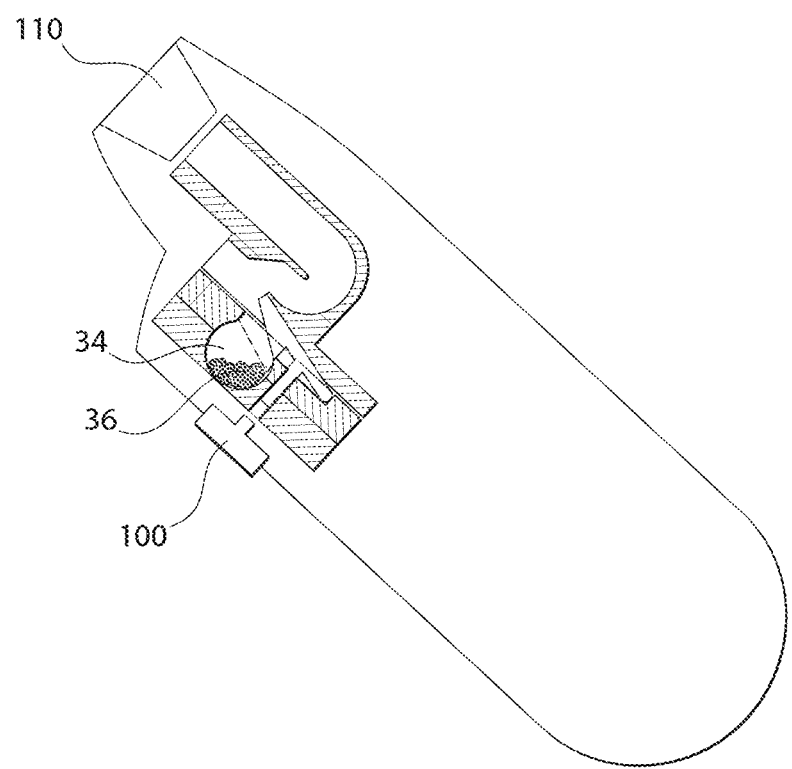

FIGS. 17*a*-17*c* show, schematically, the dispersion engine embodiment of FIGS. 14*a*-14*c*, incorporated into the multi-dose device of FIGS. 16*a*-16*c* progressively as the dose chamber is opened and moved to a subject's mouth to be dispensed. The multi-dose device of FIGS. 16*a*-16*c* is designed such that a subject naturally may hold the device in the attitude shown in FIG. 17*a*, when the subject is readying a dose to be dispensed by pressing the button on the lower side of the device. As shown in FIG. 17*a*, the cover portion and outlet channel of the device are shaped to retain dose within the chamber when held at this attitude, even after the dose chamber has been opened. This may prove beneficial for any of several reasons. First, retaining dose within the dose chamber prior to intentionally being dispersed may prevent portions or all of a dose from being lost. Additionally or alternatively, having most or all of the dose consistently in the chamber at the beginning of the delivery process may result in more consistent drug delivery characteristics. FIG. 17*b* shows the position of the powder within the dose chamber as the subject moves the multi-dose device toward their mouth to dispense the dose, and FIG. 17*c* shows the device in the attitude that subject would normally hold the device when dispensing a dose. As can be seen, the configuration of the dose chamber retains the dose as the user moves the device toward their mouth.

The U-shaped downstream portion of the air pathway is positioned to catch powder, in the bight 88 of the U that may escape from the dose chamber when opened, particularly in the attitude shown in FIG. 17*a*. This may prevent any dose that escapes the chamber from being lost prior to the dose being delivered from the device to a subject. The U-shaped portion of the pathway may additionally create turbulence that serves to further disperse dose after exiting the chamber when being dispensed to a user. It is to be appreciated that although the U-Shaped portion is shown only in connection with the embodiments of FIGS. 14*a*-14*c* and 17*a*-17*c*, that similar structures and variations thereof may be incorporated into any other embodiments. It is also to be appreciated that, according to some embodiments, a U-shaped structure or other structure that may prevent the escape of dose may be positioned upstream of the dose chamber.

Figure 18A:
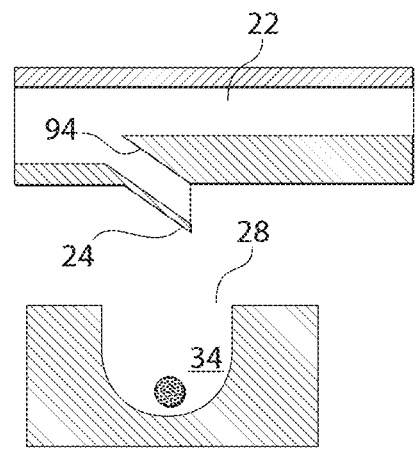
FIGS. 18a-18b show one embodiment of a delivery device that includes a dose chamber that moves relative to a cutter and air pathway to ready a dose to be dispensed.
Figure 18B:
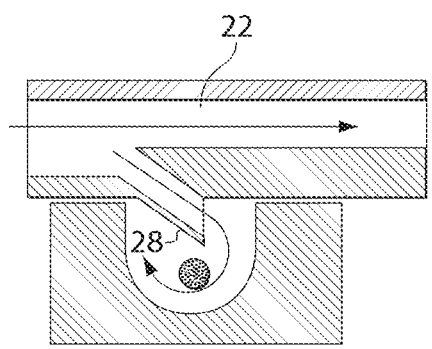

FIGS. 18*a* and 18*b* show yet another embodiment of a delivery device that includes a dose chamber and air pathway. This illustrative embodiment includes an air pathway that is integral with a cutter and structure that diverts air from the air pathway and along the cutter to a dose chamber when present. A dose chamber that is sealed on one side by a barrier may be moved into contact with the cutter (alternatively, the cutter and air pathway may be moved toward the dose chamber) to break the barrier, placing the dose chamber and air pathway in fluid communication, as shown in FIG. 18*b*. Air may then be drawn through the device to deliver a dose to a subject.

Figure 19A:
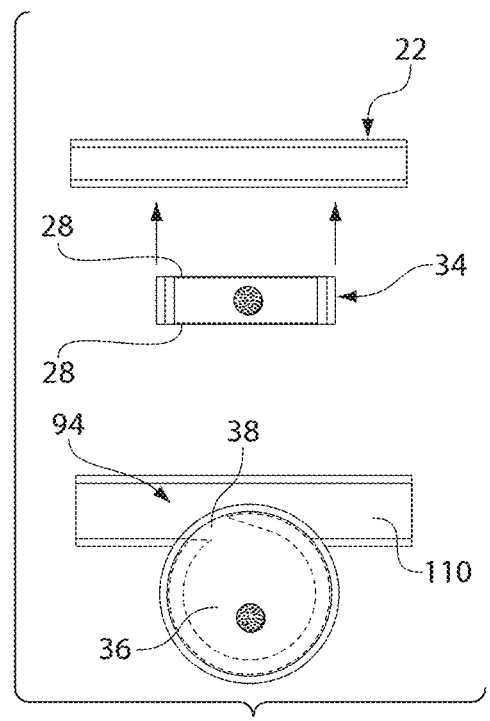
FIGS. 19a-19c show another embodiment of a delivery device that includes a dose chamber that moves relative to an air pathway to ready a dose to be dispensed.
Figure 19B:
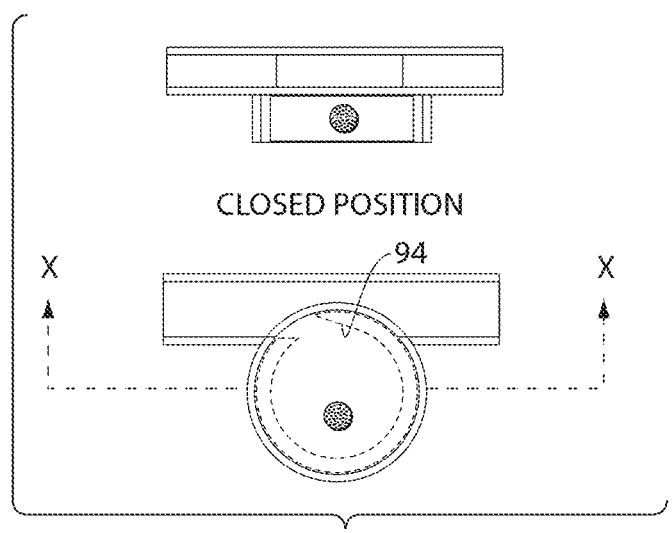
Figure 19C:
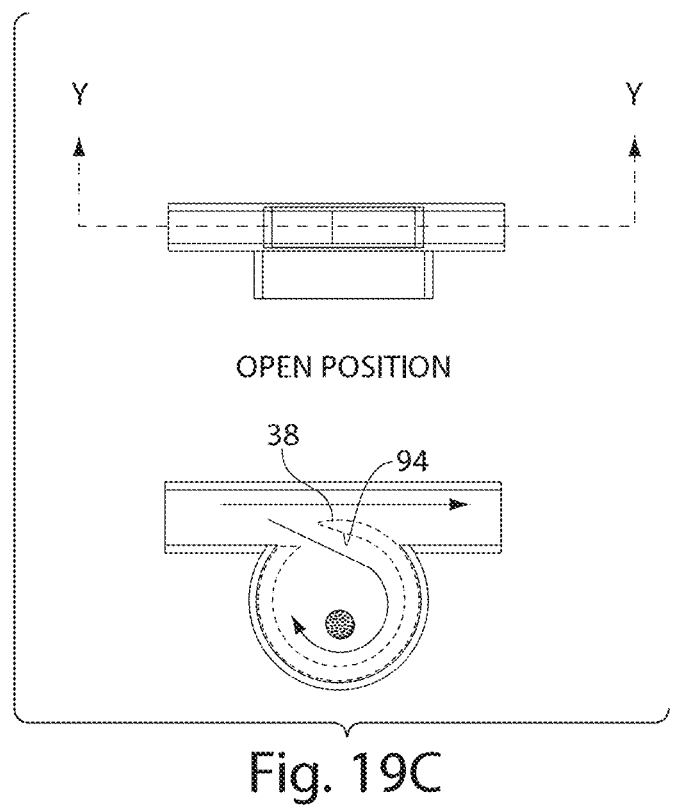

Yet another embodiment of a delivery device that includes a dose chamber that may be moved relative to an air pathway is shown in FIGS. 19*a*-19*c*. The device includes an air pathway structure that may mate with a cylindrical housing which encloses a dose chamber. The dose chamber inside of the cylindrical structure includes a diverter that directs air from the air pathway and into the dose chamber through an opening, when in a position to deliver dose to a subject. The opening of the dose chamber may be sealed by a barrier that is punctured by a cutter in the air pathway structure or on the dose chamber when the dose chamber housing is moved into the open position by translating the dose chamber housing sideways (into the page, as shown in FIG. 19*c*) to place the dose chamber and air pathway in fluid communication with one another.

In some embodiments, the devices, systems and methods may be free of secondary packaging to facilitate rapid and easy delivery of the drug when the drug needs to be delivered as fast as possible under a stressful circumstance, such as in a rescue situation.

Embodiments described herein may be configured for passive or active applications, or a combination of passive and active fluid administration. For example, each of the embodiments described herein may include use of a compressed fluid to assist in dispersing the drug.

The devices and systems described herein may be integrated into a wide variety of delivery configurations including, for example, a single-dose and multi-dose applications, in either active, passive, or active/passive applications. In addition, the devices, systems and methods may be applied to combination dose configurations and therapies.

Figure 20A:
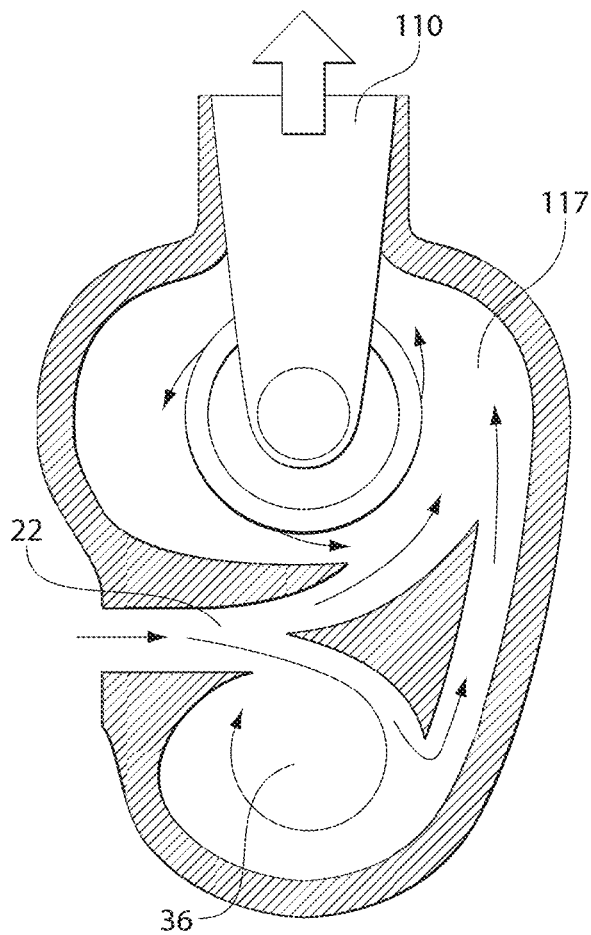
FIGS. 20a and 20b show cross-sectional views of a dose chamber, in combination with features located downstream of the dose chamber for further dispersing dose.
Figure 20B:
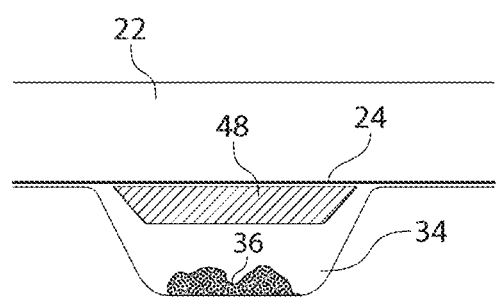
Figure 21A:
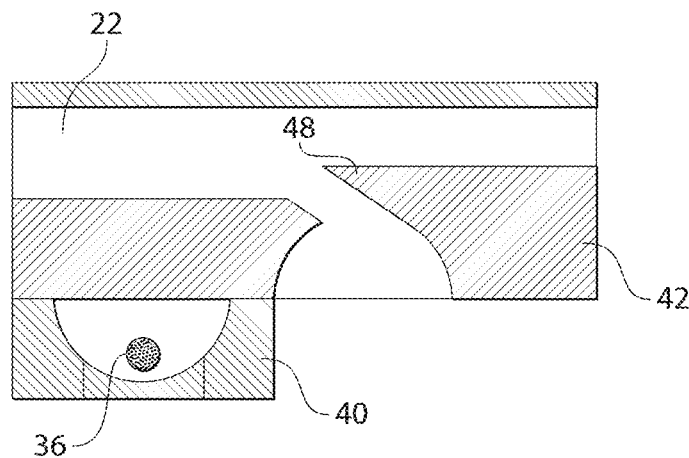
FIGS. 21a and 21b show a cross-section view of yet another embodiment of a delivery device.
Figure 21B:
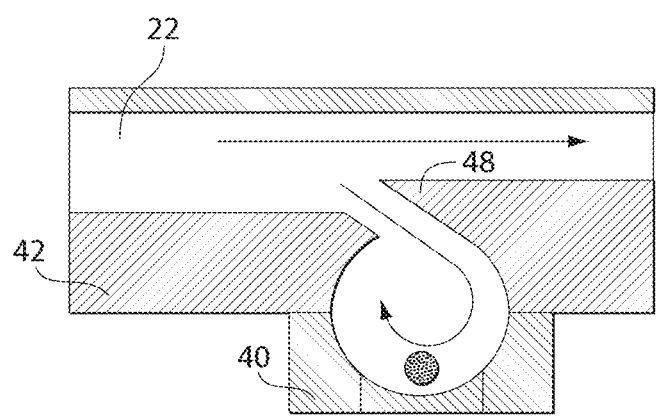

The various embodiments described herein may be used in combination with other features that promote dispersion and/or entrainment of dose in a delivery device. By way of example, FIGS. 20*a* and 20*b* show cross-sectional views of a delivery device that includes a dose chamber, and a dispersion device, positioned downstream from the dose chamber. In use, air is drawn into the air inlet, toward a stationary diverter. The diverter directs a portion of the air toward the dose chamber, and the remaining air moves directly toward the downstream dispersion device. The dose chamber, as shown in FIG. 20*b*, includes a blister pack with a cutter positioned internally therein, as described in U.S. patent application Ser. No. 61/285,161, filed Dec. 9, 2009, which is hereby incorporated by reference in its entirety. After dose has been entrained, the dose laden air moves to the downstream dispersion device where further mixing and dispersion occur. Additionally, a portion of the air moves directly to the dispersion chamber from the dose chamber through a bypass. The downstream dispersion device shown in FIG. 20*a*, is configured to have a torus shape. Air enters the dispersion device from a central location, and swirls circumferentially about the torus shaped chamber, allowing air and dispersed particles to exit the chamber through a central portion, similar to dispersion devices discussed with respect to some embodiments of U.S. patent application Ser. No. 61/285,161. It is to be appreciated that the embodiment of FIGS. 20*a* and 20*b* show but one type of downstream dispersion device, and that others are also possible and contemplated. By way of example, according to other embodiments, dispersion devices may include swirl chambers, mesh screens, rotors, classifiers, piezoelectric dispersion devices, and the like.

FIGS. 21*a* and 21*b* show yet another embodiment that includes a dose chamber located in a lower housing that slides between a first position, where the dose chamber is closed, and a second position where the dose chamber is open to a primary air pathway. The primary air pathway is located in an upper housing, and includes a stationary diverter that directs air flow to the dose chamber. The dose chamber of the lower housing may be sealed to the upper chamber by virtue of a direct sealing between the upper and lower housings (e.g. plastic-on-plastic), according to some embodiments. According to other embodiments, a barrier material may seal the dose chamber, and may be pealed away from the dose chamber during movement of the lower housing.

The devices, systems and methods described herein may be used to deliver materials, other than a drug/medicament, to the body. The materials may be delivered through the mouth or nose and into the oral cavity, nasal cavity, and/or to the lungs. Materials that are intended to be delivered into the oral cavity include, for example, nutritional compositions (such as sugars, candy, food, vitamins, and quick energy supplements in liquid and/or powder (e.g., nanoparticles) form) and non-nutritional compositions (such as flavorants (e.g., esters)). Other materials that may be delivered into the oral cavity include those used for oral hygiene and dental treatment (e.g., breath fresheners, fluoride treatments, teeth whiteners, anti-bacterial compositions, mouthwashes). Drugs and related compositions (such as anesthetics, therapeutic markers) may also be delivered into the oral cavity. Materials that the may be inhaled into the lungs include, for example, drugs (e.g., for treating asthma, bronchitis, pneumonia) and therapeutic markers (such as dyes, scanning agents, radio labeling or tagging agents, UV labeling agents, contrasts agents in liquid and/or powder (e.g., nanoparticles) form). In this respect, it is to be appreciated that any of the above materials may be used in the devices, systems, and methods described herein in place of drug(s)/medicaments. It is also to be appreciated that the terms "drug" and "medicament" are used interchangeable herein, and include any of the foregoing compositions and any others, whether in powder, liquid or other form, that may be delivered to a human or animal for therapeutic, diagnostic, or other effect. In certain aspects, the delivery device is configured for use with other entranceways into a human or animal body, whether naturally formed or created otherwise, and with aspects of the human or animal body other than the respiratory system. Although the embodiments described incorporate air as the fluid for delivering the medicament, other fluids are contemplated as should be apparent to one of skill in the art.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A delivery device comprising:

a primary air pathway having an upstream portion and a downstream portion;

a dose chamber having an opening that, when opened, places the dose chamber and the primary pathway in fluid communication at a position between the upstream portion and the downstream portion; and a cover that, in a first position over the opening, closes fluid communication between the dose chamber and the primary air pathway and that moves to a second position to selectively open fluid communication between the dose chamber and the primary air pathway through the opening, the cover being positioned to divert air to the dose chamber from the upstream portion of the air pathway when in the second position.

2. The delivery device of claim 1, further comprising:

a moisture barrier that seals the opening.

3. The delivery device of claim 2, further comprising:

a cutter that breaks the moisture barrier when the cover pivots to the second position to selectively open fluid communication between the dose chamber and the primary air pathway.

4. The delivery device of claim 3, wherein the cutter is a part of the cover.

5. The delivery device of claim 3, wherein the cutter is mounted to the moisture barrier.

6. The delivery device of claim 5, wherein the cutter is mounted to a dose chamber side of the barrier.

7. The delivery device of claim 5, wherein the cutter is mounted to an air pathway side of the barrier.

8. The delivery device of claim 3, wherein the cutter includes a feature to increase pressure at an area of the moisture barrier when the cutter breaks the moisture barrier.

9. The delivery device of claim 1, wherein the primary air pathway includes a restriction to increase the velocity of air flowing through central portions of the air pathway.

10. The delivery device of claim 1, further comprising:

a bypass that places the dose chamber in fluid communication with the downstream portion of the air pathway.

11. The delivery device of claim 1, wherein cover is positioned in the way of air that is returning to the air pathway from the dose chamber to promote recirculation of air in the dose chamber.

12. The delivery device of claim 1, further comprising:

an air outlet that leads from the opening of the dose chamber to the primary air pathway.

13. The delivery device of claim 1, further comprising:

a dose of medicament in the dose chamber.

14. The delivery device of claim 1, wherein the cover moves from the first position to the second position by pivoting.

15. The delivery device of claim 1, further comprising a dispersion device positioned downstream of the dose chamber.

16. A multi-dose device including a plurality of delivery devices according to claim 1.

17. The multi-dose device of claim 16, comprising a housing with an outlet arranged to be placed, sequentially, in fluid communication with the primary air pathway of the plurality of delivery devices.

18. The multi-dose device of claim 17, further comprising an actuator to open the cover of a delivery device in fluid communication with the outlet.

19. The delivery device of claim 1, wherein the cover includes a diverter that faces in the upstream direction with the cover in the second position to direct a portion of air in the primary air pathway into the dose chamber.

* * * * *